US009913840B2

(12) United States Patent
Jain et al.

(10) Patent No.: US 9,913,840 B2
(45) Date of Patent: Mar. 13, 2018

(54) FORMULATIONS FOR ARIPIPRAZOLE DELIVERY TRANSDERMALLY

(71) Applicant: Corium International, Inc., Menlo Park, CA (US)

(72) Inventors: Amit K. Jain, Milpitas, CA (US); Eun Soo Lee, Redwood City, CA (US); Parminder Singh, Union City, CA (US)

(73) Assignee: Corium International, Inc., Menlo Park, CA (US)

( * ) Notice: Subject to any disclaimer, the term of this patent is extended or adjusted under 35 U.S.C. 154(b) by 0 days.

(21) Appl. No.: 15/176,080

(22) Filed: Jun. 7, 2016

(65) Prior Publication Data

US 2016/0354369 A1  Dec. 8, 2016

Related U.S. Application Data

(60) Provisional application No. 62/172,610, filed on Jun. 8, 2015.

(51) Int. Cl.
*A61K 31/496* (2006.01)
*A61K 47/10* (2017.01)
*A61K 47/12* (2006.01)
*A61K 47/14* (2017.01)
*A61K 47/20* (2006.01)
(Continued)

(52) U.S. Cl.
CPC .......... *A61K 31/496* (2013.01); *A61K 9/0014* (2013.01); *A61K 47/06* (2013.01); *A61K 47/10* (2013.01); *A61K 47/12* (2013.01); *A61K 47/14* (2013.01); *A61K 47/20* (2013.01); *A61K 47/22* (2013.01); *A61K 47/32* (2013.01); *A61K 47/38* (2013.01)

(58) Field of Classification Search
CPC ...... A61K 31/496; A61K 47/06; A61K 47/10; A61K 47/12; A61K 47/14; A61K 47/20; A61K 47/22; A61K 47/32; A61K 47/38; A61K 9/0014
See application file for complete search history.

(56) References Cited

U.S. PATENT DOCUMENTS 5,006,528 A  4/1991  Oshiro et al.
8,815,261 B2  8/2014  Hanma
(Continued)

FOREIGN PATENT DOCUMENTS

GB  2505859 A  3/2014
GB  2505860 A  3/2014
(Continued)

OTHER PUBLICATIONS

Zhang et al. (AAPS pharmaSciTech vol. 11, No. 2, 2010, pp. 894-903).*
(Continued)

*Primary Examiner* — Savitha M Rao
(74) *Attorney, Agent, or Firm* — Judy Mohr; Wen Li; McDermott Will & Emery LLP

(57) ABSTRACT

Formulations for topical application of aripiprazole are provided. The formulations, when applied topically to the skin of a subject, provide a therapeutic amount of aripiprazole in the blood for a sustained period of time for treatment of conditions responsive to aripiprazole including but not limited to depression, schizophrenia, and bipolar disorder.

13 Claims, 4 Drawing Sheets

Formulation 13

(51) Int. Cl.
*A61K 47/22* (2006.01)
*A61K 47/32* (2006.01)
*A61K 47/38* (2006.01)
*A61K 9/00* (2006.01)
*A61K 47/06* (2006.01)

(56) References Cited

U.S. PATENT DOCUMENTS

| | | |
|---|---|---|
| 2004/0170672 A1* | 9/2004 | Selzer .................. A61K 31/496 424/449 |
| 2012/0184563 A1 | 7/2012 | Hanma |
| 2013/0171237 A1 | 7/2013 | Plakogiannis et al. |

FOREIGN PATENT DOCUMENTS

| | | | |
|---|---|---|---|
| WO | W2012/058091 | * | 5/2012 |
| WO | WO 2014/060324 A1 | | 4/2014 |

OTHER PUBLICATIONS

International Search Report from PCT Patent Application No. PCT/US2016/036248 dated Aug. 9, 2016.

* cited by examiner

FORMULATIONS FOR ARIPIPRAZOLE DELIVERY TRANSDERMALLY

CROSS-REFERENCE TO RELATED APPLICATIONS

This application claims the benefit of U.S. Provisional Application No. 62/172,610, filed Jun. 8, 2015, incorporated herein by reference in its entirety

TECHNICAL FIELD

The subject matter described herein relates to compositions comprising aripiprazole, and to methods for delivering aripiprazole to a patient in need.

BACKGROUND

Aripiprazole which has the structure is an atypical antipsychotic agent useful in treating schizophrenia. It has poor aqueous solubility, with a solubility of less than about 1 microgram/mL (μg/mL) at room temperature. Aripiprazole is a dopamine $D_2$ and serotonin $5\text{-}HT_{1A}$ receptor agonist and antagonist of the serotonin $5\text{-}HT_{2A}$ receptor. Aripiprazole is used to treat schizophrenia and other psychotic and CNS disorders. See, for example, U.S. Pat. No. 5,006,528. The drug is currently sold as a tablet for oral administration. However, poor patient compliance with oral antipsychotics has been reported. As such, there exists a need for compositions and methods of delivering antipsychotics, such as aripiprazole, thereby improving patient compliance and maximizing the pharmacological profile of the active agent.

The foregoing examples of the related art and limitations related therewith are intended to be illustrative and not exclusive. Other limitations of the related art will become apparent to those of skill in the art upon a reading of the specification and a study of the drawings.

BRIEF SUMMARY

The following aspects and embodiments thereof described and illustrated below are meant to be exemplary and illustrative, not limiting in scope.

In one aspect, a composition for topical or transdermal administration of aripiprazole is provided. The composition comprises aripiprazole and a vehicle consisting essentially of glycerol; a glycol; lauryl lactate; lactic acid; water or a surfactant; and a polymeric vehicle.

In one embodiment, the amount of aripiprzole in the composition is between about 0.5-50 wt %. In another embodiment, aripiprazole is present in the composition in an amount between about 1-25 wt %.

In one embodiment, glycerol is present in an amount between 5-25 wt %.

In another embodiment, a glycol is present in the formulation in a total amount of between 15-50 wt %.

In another embodiment, the glycol is hexylene glycol, propylene glycol, or a mixture of hexylene glycol, propylene glycol. In one embodiment, the mixture comprises hexylene glycol and propylene glycol in a ratio of between about 1:1 to 1:0.5.

In yet another embodiment, hexylene glycol is present in the vehicle in an amount between 3-30 wt %. In still another embodiment, propylene glycol is present in the vehicle in an amount between 3-30 wt %.

In one embodiment, lauryl lactate is present in an amount between about 0.5-10 wt %.

In another embodiment, lactic acid is present in an amount between 0.5-10 wt %.

In still another embodiment, the polymeric vehicle is selected from the group consisting of a polyvinylpyrrolidone, a hydroxyalkylcellulose and a polyacrylate copolymer.

In one embodiment, the polymeric vehicle is a hydroxyalkylcellulose is selected from hydroxymethylcellulose, hydroxyethylcellulose, and hydroxypropylcellulose. In one embodiment, embodiment, the hydroxyalkylcellulose is in an amount to function as a gelling agent or thickening agent in the composition.

In another embodiment, the polyvinylpyrrolidone is selected from polyvinylpyrrolidone homopolymers and polyvinylpyrrolidone copolymers.

In yet another embodiment, the polyacrylate copolymer is a copolymer of methacrylic acid and methyl methylacrylate monomers. In one embodiment, the copolymer is poly (methacylic acid-co-methyl methacrylate) having a 1:1 ratio of the monomers (Eudragit L-100).

In still another embodiment, the surfactant is a sorbitan monolaurate.

In another embodiment, the water or the surfactant is present in an amount between about 3-15 wt %.

In another embodiment, the formulation, composition or vehicle further comprises or consists of dimethyl sulfoxide.

In another aspect, a formulation consisting essentially of the following components is provided: between about 1-12 wt %; aripiprazole; between about 18-22 wt % dimethyl sulfoxide; between about 5-40 wt % of a glycol selected from hexylene glycol, propylene glycol, or a mixture thereof; between about 5-20 wt % glycerol; between about 0.5-10 wt % lauryl lactate; between about 0.5-10 wt % lactic acid; between about 2-15 wt % water or a surfactant; and a polymeric vehicle.

In one embodiment, the surfactant is a sorbitan monolaurate.

In another embodiment, the polymeric vehicle is present in an amount between 20-40 wt %. In another embodiment, the polymeric vehicle is present in an amount between 20-35 wt %. In another embodiment, the polymeric vehicle is present in an amount between 5-40 wt %. In another embodiment, the polymeric vehicle is present in an amount between 5-35 wt %.

In yet another embodiment, the polymeric vehicle comprises a combination of a polyvinylpyrrolidone and a hydroxyalkylcellulose.

In still another embodiment, the polymeric vehicle comprises a copolymer of methacrylic acid and methyl methylacrylate monomers.

In another embodiment, the hydroxyalkylcellulose is selected from hydroxymethylcellulose, hydroxyethylcellulose, and hydroxypropylcellulose.

In another aspect, a formulation consisting essentially of the following components is provided: between about 1-12 wt %; aripiprazole; between about 5-40 wt % of a glycol selected from hexylene glycol, propylene glycol, or a mixture thereof; between about 10-25 wt % glycerol; between about 0.5-10 wt % lauryl lactate; between about 0.5-10 wt % lactic acid; between about 2-15 wt % water or a surfactant; and between 20-35 wt % of a polymeric vehicle comprising a polyvinylpyrrolidone or a hydroxyalkylcellulose or both.

In another aspect, a formulation consisting essentially of the following components is provided: between about 1-12 wt %; aripiprazole; between about 5-40 wt % of a glycol selected from hexylene glycol, propylene glycol, or a mixture thereof; between about 10-25 wt % glycerol; between about 0.5-10 wt % lauryl lactate; between about 0.5-10 wt % lactic acid; between about 2-15 wt % water or a surfactant; and between 5-35 wt % of a polymeric vehicle comprising a polyvinylpyrrolidone or a hydroxyalkylcellulose or both.

In yet another aspect, a method for administration of aripiprazole is provided. The method comprises applying to the skin of a subject in need a composition, formulation, vehicle or delivery device comprising the composition, formulation, or vehicle.

In another aspect, a method for treating depression, schizophrenia, bipolar disorder, dementia, irritability, agitation associated with schizophrenia or bipolar disorder, Tourette's disorder is provided. The method comprises applying or providing a composition, a formulation, a vehicle or a delivery device comprising the composition, formulation, or vehicle described herein. Where the method comprises providing, said providing is in conjunction with instructions to apply to the skin of a subject in need.

In another aspect, a method for treating a condition responsive to aripiprazole is provided. The method comprises applying or providing a composition, formulation, vehicle or delivery device comprising the composition, formulation, or vehicle. Where the method comprises providing, said providing is in conjunction with instructions to apply to the skin of a subject in need.

In one embodiment, the methods provide an amount of aripiprazole in the blood of the subject effective for therapy for a period of at least about 1 day, 3 days, 4 days, 5 days, 6 days or 7 days.

In another aspect, a transdermal delivery device comprising the composition, formulation, or vehicle described herein is provided.

In addition to the exemplary aspects and embodiments described above, further aspects and embodiments will become apparent by reference to the drawings and by study of the following descriptions.

Additional embodiments of the present methods and compositions, and the like, will be apparent from the following description, drawings, examples, and claims. As can be appreciated from the foregoing and following description, each and every feature described herein, and each and every combination of two or more of such features, is included within the scope of the present disclosure provided that the features included in such a combination are not mutually inconsistent. In addition, any feature or combination of features may be specifically excluded from any embodiment of the present invention. Additional aspects and advantages of the present invention are set forth in the following description and claims, particularly when considered in conjunction with the accompanying examples and drawings.

DETAILED DESCRIPTION

I. Definitions

Figure 1:
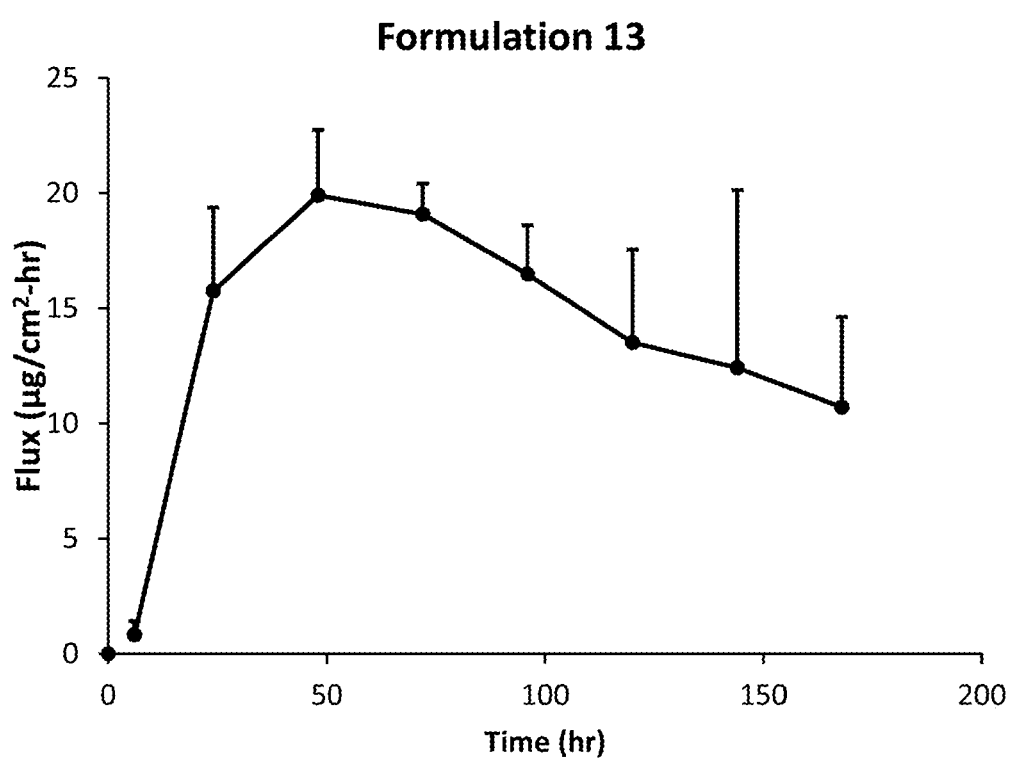
FIG. 1 is a graph of aripiprazole flux, in $\mu g/cm^2 \cdot hr$, in vitro as a function of time, in hours, in an in vitro skin permeation test from a formulation identified herein as formulation no. 13.
Figure 2:
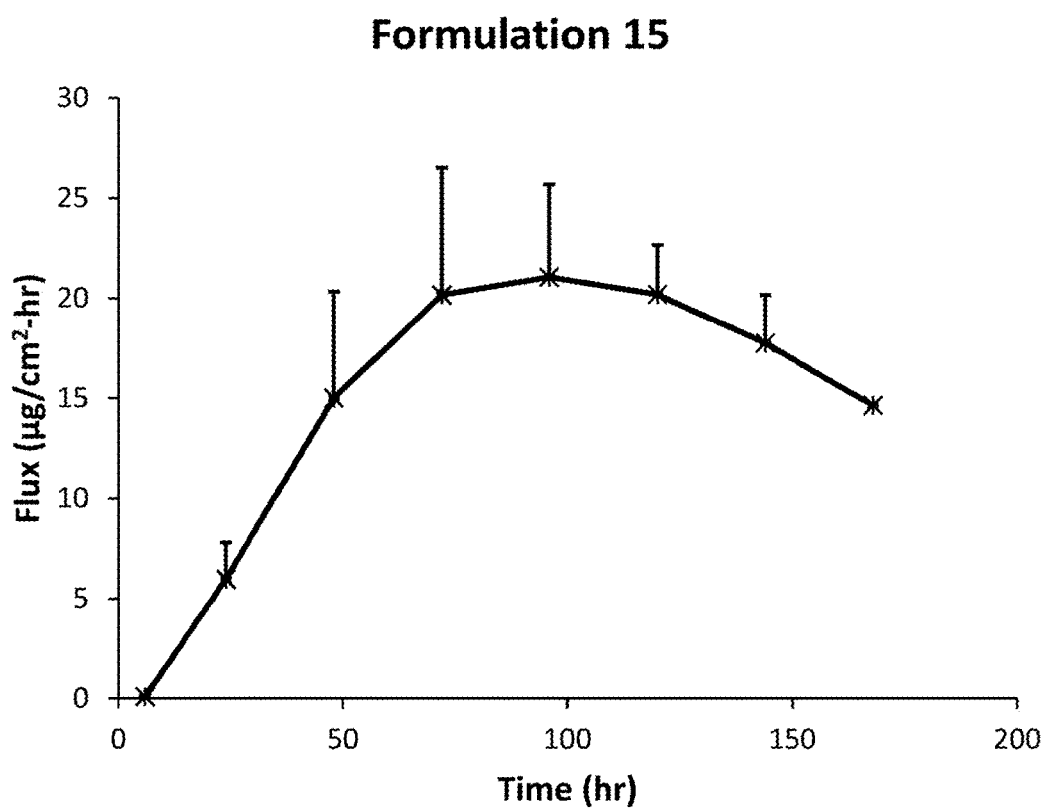
FIG. 2 is a graph of aripiprazole flux, in $\mu g/cm^2 \cdot hr$, in vitro as a function of time, in hours, in an in vitro skin permeation test from a formulation identified herein as formulation no. 15.
Figure 3:
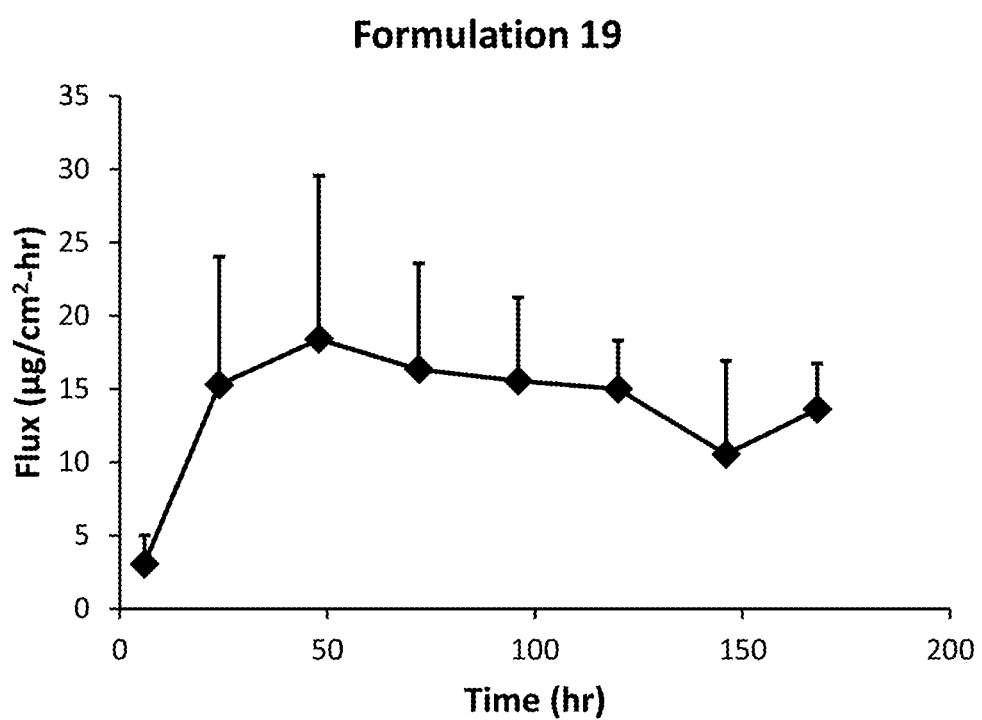
FIG. 3 is a graph of aripiprazole flux, in $\mu g/cm^2 \cdot hr$, in vitro as a function of time, in hours, in an in vitro skin permeation test from a formulation identified herein as formulation no. 19.

Various aspects now will be described more fully hereinafter. Such aspects may, however, be embodied in many different forms and should not be construed as limited to the embodiments set forth herein; rather, these embodiments are provided so that this disclosure will be thorough and complete, and will fully convey its scope to those skilled in the art.

Where a range of values is provided, it is intended that each intervening value between the upper and lower limit of that range and any other stated or intervening value in that stated range is encompassed within the disclosure. For example, if a range of 1 μm to 8 μm is stated, it is intended that 2 μm, 3 μm, 4 μm, 5 μm, 6 μm, and 7 μm are also explicitly disclosed, as well as the range of values greater than or equal to 1 μm and the range of values less than or equal to 8 μm.

As used in this specification, the singular forms "a," "an," and "the" include plural referents unless the context clearly dictates otherwise. Thus, for example, reference to a "polymer" includes a single polymer as well as two or more of the same or different polymers, reference to an "excipient" includes a single excipient as well as two or more of the same or different excipients, and the like.

II. Formulations

Formulations for topical application for transdermal delivery of aripiprazole are provided. The formulations provide delivery of aripiprazole transdermally in an amount sufficient for therapy for conditions responsive to aripiprazole. Exemplary formulations were prepared and are described in Example 1.

In one embodiment, a formulation is provided, where the formulation comprises aripiprazole and a delivery vehicle that consists or consists essentially of glycerol; a glycol; lauryl lactate; lactic acid; water or a surfactant; and a polymeric vehicle.

Aripiprazole is typically included in the formulation in an amount between 1-25 wt %. Aripiprazole is present in the formulation as a base, in one embodiment. Salt forms of aripiprazole are contemplated.

The components of the delivery vehicle are tailored to provide transdermal absorption of aripiprazole in an amount sufficient for therapy for a period of at least about 1 day, 3 days, 4 days, 5 days, 6 days or 7 days; alternatively for a period of between about 3-7 days, 4-7 days, 5-7 days or 6-7 days. The components of the delivery vehicle that provide release for this period are now described.

Glycerol is present in the delivery vehicle or formulation in an amount between 5-25 wt %, or between about 8-20 wt % or between about 8-18 wt %. In the formulations prepared and tested for in vitro permeation described herein glycerol was present in amounts of 10 wt %, 11 wt %, 13-13.5 wt % and 15-15.5 wt %.

A glycol is present in the delivery vehicle or formulation in a total amount of between 15-50 wt %. In one embodiment, the glycol is hexylene glycol (2-methyl-2,4-pentanediol), propylene glycol, or a mixture of hexylene glycol, propylene glycol. Typically, the mixture comprises hexylene glycol and propylene glycol in a ratio of between about 1:1 to 1:0.5. Hexylene glycol is present in the vehicle or formulation, in one embodiment, in an amount between 3-30 wt %. Propylene glycol is present in the vehicle or formulation in an amount between 3-30 wt %. In the formulations and vehicles prepared and tested for in vitro permeation described herein a mixture of hexylene glycol and propylene glycol was included, where the ratio of hexylene glycol to propylene glycol was 1:0.9, 1:0.94, 1:0.65 and 1:0.67. Stated alternatively, the amount of hexylene glycol in the formulations and vehicles was about 11 wt %, about 12wt %, and about 15wt %. The amount of propylene glycol in the formulations and vehicles described herein was about 7 wt %, about 8 wt %, about 13 wt % and about 14 wt %. It will be appreciated that other glycols may be suitable, such as dipropylene glycol and tripropylene glycol.

The formulations and vehicles also comprise lauryl lactate in an amount between about 0.5-10 wt %. The amount of lauryl lactate in the formulations and vehicles described herein was about 2 wt % or about 4 wt %.

Lactic acid is included in the formulations and vehicles in an amount between 0.5-10 wt % or between about 1-7 wt % or between about 1.5-5.5 wt %. In one embodiment, the molar ratio of lactic acid to aripiprazole is not from 0.5:1 to 3:1. In another embodiment, the molar ratio of lactic acid to aripiprazole is between 0.5:1 to 3:1 and the formulation or delivery vehicle does not include N,N-dimethylformamide, N,N-dimethylacetamide, or N-methyl-2-pyrrolidone or does not include isopropyl myristate, diethyl sebacate, medium-chain triglyceride, propylene carbonate. In the exemplary formulations and vehicles prepared herein, lactic acid was included at about 2 wt % and at about 5 wt %.

A polymeric vehicle is present in the formulation or vehicle. In one embodiment, the polymeric vehicle is a polyvinylpyrrolidone or a hydroxyalkylcellulose or a polyacrylate copolymer. In another embodiment the polymeric vehicle is a combination of a polyvinylpyrrolidone or a hydroxyalkylcellulose. In another embodiment, the polymeric vehicle is a mixture of a hydroxyalkylcellulose and at least one or both of a polyvinylpyrrolidone and a polyacrylate copolymer.

In one embodiment, the hydroxyalkylcellulose is selected from hydroxymethylcellulose, hydroxyethylcellulose, and hydroxypropylcellulose. In one embodiment, the hydroxyalkylcellulose functions as a gelling agent or thickening agent and is present in the vehicle or composition in an amount sufficient to achieve this function.

The polyvinylpyrrolidone is selected from polyvinylpyrrolidone homopolymers and polyvinylpyrrolidone copolymers. A polyvinylpyrrolidone homopolymer with an average molecular weight of about 40,000 Daltons is included in the formulation or vehicle, in one embodiment.

The polyacrylate copolymer is, in one embodiment, a copolymer of methacrylic acid and methyl methylacrylate monomers. In one embodiment, the copolymer is poly (methacylic acid-co-methyl methacrylate) having a 1:1 ratio of the monomers (Eudragit L-100).

The formulation or vehicle also comprises water or a surfactant as an optional component. In one embodiment, the optional water or the surfactant is present, and is present in an amount between about 3-15 wt %. The surfactant when present is, in one embodiment, a sorbitan monolaurate.

The formulation, composition or vehicle further comprises or consists of dimethyl sulfoxide, in one embodiment. When present, DMSO is included in an amount between about 15-25 wt %, preferably between about 18-22 wt %.

The formulation, composition or vehicle may further comprise oleic acid or another fatty acid, in some embodiments. When present, a fatty acid, such as oleic acid, is present in an amount between about 1-10 wt %, or 2-8 wt % or 2-6 wt %.

In another aspect, a formulation consisting essentially of the following components is provided: between about 1-12 wt %; aripiprazole; between about 5-40 wt % of a glycol selected from hexylene glycol, propylene glycol, or a mixture thereof; between about 10-25 wt % glycerol; between about 0.5-10 wt % lauryl lactate; between about 0.5-10 wt % lactic acid; between about 2-15 wt % water or a surfactant; and between about 5-40 wt %, or between about 5-35 wt %, or between about 20-35 wt %, or between about 20-40 wt % of a polymeric vehicle comprising a polyvinylpyrrolidone or a hydroxyalkylcellulose or both.

Figure 4:
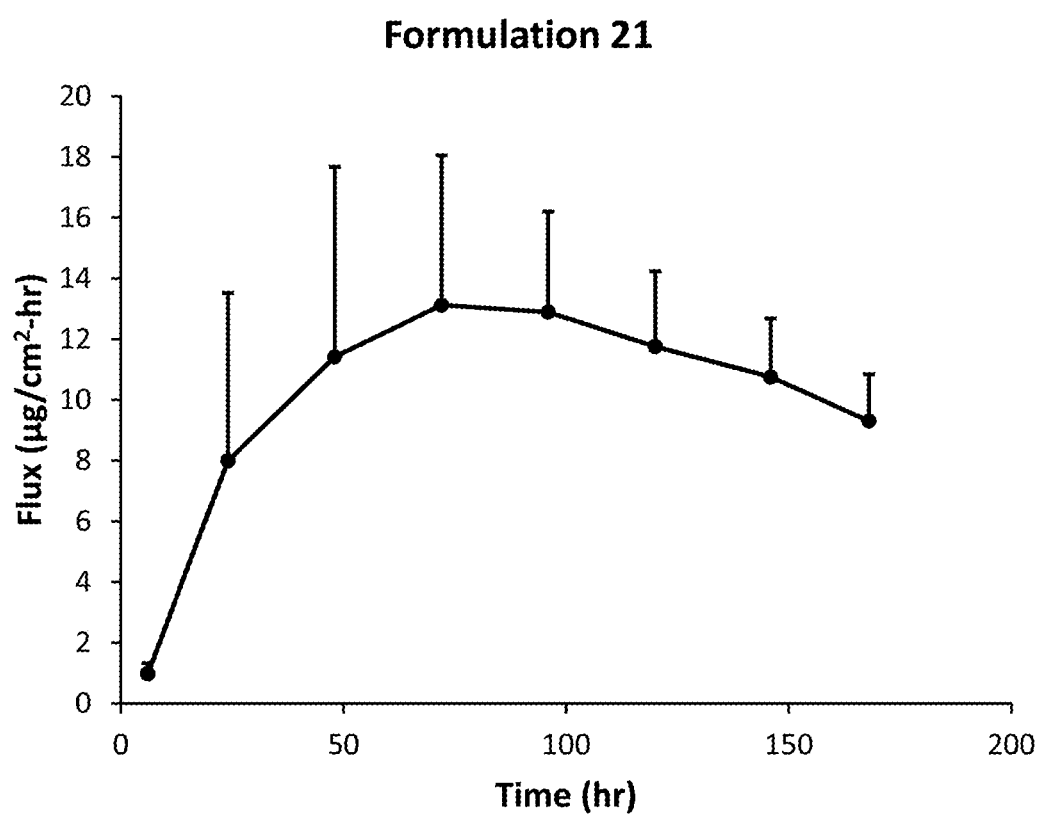
FIG. 4 is a graph of aripiprazole flux, in $\mu g/cm^2 \cdot hr$, in vitro as a function of time, in hours, in an in vitro skin permeation test from a formulation identified herein as formulation no. 21.

Formulations prepared with the components described above were tested for in vitro skin flux. FIGS. 1-4 are graphs showing the flux of the formulations identified herein as formulation no. 13 (FIG. 1), formulation no. 15 (FIG. 2), formulation no. 19 (FIG. 3) and formulation no. 21 (FIG. 4).

The in vitro skin flux of aripiprazole provided by the formulations described herein is between about 10-20 $\mu g/cm^2 \cdot hr$ at steady state, which is typically reached within about 48 hours of topical application. The steady state flux is maintained for a period of at least about 3 days or at least about 4 days. Accordingly, the formulations provide a means for administration of aripiprazole transdermally in a device or composition that lasts for at least about 1 day, 3 days, or at least about 4 days, or at least about 5, 6, or 7 days. In one embodiment, the formulation is applied topically to the skin of a subject and achieves transdermal administration of aripiprazole as evidenced by aripiprazole concentration in the blood of the subject.

III. Methods of Treatment

A method for treating a condition responsive to aripiprazole is contemplated, where a formulation as described herein is provided along with instructions to apply the formulation to skin of a subject in need. In some embodiments, the condition responsive to aripiprazole is depression, schizophrenia, or bipolar disorder. The formulations described herein can, of course, be applied directly to the skin or can be incorporated into a transdermal patch that comprises a backing layer and other materials as needed, such as a porous membrane, an adhesive. When incorporated into a patch, it is desired that the materials be non-rate limiting to aripiprazole permeation, so that the device permits release of aripiprazole from the formulation to achieve an aripiprazole concentration in the blood sufficient for therapy for a period of at least about 1 day, 3 days, 4, days, 5 days, 6 days or 7 days. In another embodiment, the materials of the transdermal patch, such as a microporous membrane positioned between the skin and the reservoir in which the aripiprazole formulation is retained, influences or controls aripiprazole permeation from the device. In this embodiment, the device provides an aripiprazole concentration in the blood sufficient for therapy for a period of at least about 1 day, 3 days, 4, days, 5 days, 6 days or 7 days.

IV. Examples

The following examples are illustrative in nature and are in no way intended to be limiting.

EXAMPLE 1

Topical Formulations Comprising Aripiprazole

Formulations were prepared to comprise the following ingredients.

Formulation 13

| Material | % w/w |
|---|---|
| Aripiprazole | 7.00% |
| Dimethyl sulfoxide (DMSO) | 20.00% |
| Hexylene glycol | 15.00% |
| Propylene glycol | 13.00% |
| Glycerol | 11.00% |
| Lauryl lactate (Ceraphyl 31) | 4.00% |
| Lactic acid | 5.00% |
| Span 20 | 5.00% |
| PVP K-30 | 15.00% |
| HPC, HF | 5.00% |
| Total | 100.00% |

Formulation 15

| Materials | % w/w |
|---|---|
| Aripiprazole | 7.00% |
| Hexylene glycol | 15.33% |
| Propylene glycol | 14.33% |
| Glycerol | 15.34% |
| Lauryl lactate (Ceraphyl 31) | 4.00% |
| Lactic acid | 5.00% |
| Water | 8.00% |
| PVP K-30 | 26.00% |
| HPC, HF | 5.00% |
| Total | 100.00% |

Formulation 19

| Materials | % w/w |
|---|---|
| Aripiprazole | 7.00% |
| Dimethyl sulfoxide (DMSO) | 20.00% |
| Hexylene glycol | 11.33% |
| Propylene glycol | 7.33% |
| Glycerol | 13.34% |
| Lauryl lactate (Ceraphyl 31) | 2.00% |
| Lactic acid | 2.00% |
| Water | 8.00% |
| Eudragit L100-55 | 3.00% |
| PVP K-30 | 21.00% |
| HPC, HF | 5.00% |
| Total | 100.00% |

Formulation 21

| Materials | % w/w |
|---|---|
| Aripiprazole | 7.00% |
| Dimethyl sulfoxide (DMSO) | 20.00% |
| Hexylene glycol | 12.00% |
| Propylene glycol | 8.00% |
| Glycerol | 10.00% |
| Lauryl lactate (Ceraphyl 31) | 4.00% |
| Lactic acid | 5.00% |
| Water | 8.00% |
| Eudragit L100-55 | 3.00% |
| PVP K-30 | 18.00% |
| HPC, HF | 5.00% |
| Total | 100.00% |

EXAMPLE 2

In Vitro Skin Permeation

Formulations prepared as described in Example 1 were tested in vitro for skin flux. The results are shown in FIGS. 1-4.

EXAMPLE 3

Transdermal Aripiprazole Formulations

Additional formulations were prepared as set forth below.

| | Formulation No. 6 | Formulation No. 8 |
|---|---|---|
| Aripiprazole | 7.30% | 7.00% |
| Dimethylsulfoxide (DMSO) | 19.6% | 0.00% |
| Hexylene Glycol | 7.91% | 17.00% |
| Propylene glycol | 8.02% | 11.75% |
| Span 20 (Sorbitan monolaurate) | 5.13% | 0.00% |
| Lauryl lactate | 5.87% | 6.00% |
| Glycerine | 7.94% | 15.00% |
| Oleic acid | 3.91% | 4.00% |
| Lactic acid | 4.92% | 5.00% |
| Hydroxypropyl cellulose GF | 4.89% | 0.00% |
| Water | 9.84% | 8.25% |
| PVP K30 (Polyvinyl pyrrolidone K 30) | 14.67% | 26.00% |
| Total | 100% | 100% |

While a number of exemplary aspects and embodiments have been discussed above, those of skill in the art will recognize certain modifications, permutations, additions and sub-combinations thereof. It is therefore intended that the following appended claims and claims hereafter introduced are interpreted to include all such modifications, permutations, additions and sub-combinations as are within their true spirit and scope.

It is claimed:

1. A transdermal formulation consisting essentially of:
   between about 1-12 wt %; aripiprazole;
   between about 15-25 wt % dimethyl sulfoxide;
   between about 5-40 wt % of a glycol selected from hexylene glycol, propylene glycol, or a mixture thereof;

between about 5-20 wt % glycerol;
between about 0.5-10 wt % lauryl lactate;
between about 0.5-10 wt % lactic acid;
optionally between about 2-15 wt % water or a surfactant; and
a polymeric vehicle,
wherein the formulation does not comprise any selected from N,N-dimethylformamide, N,N-dimethylacetamide, N-methyl-2-pyrrolidone, isopropyl myristate, diethyl sebacate, medium-chain triglyceride, and propylene carbonate.

2. The formulation of claim 1, wherein the surfactant is a sorbitan monolaurate.

3. The formulation of claim 1, wherein the polymeric vehicle is present in an amount between 5-40 wt %.

4. The formulation of claim 3, wherein the polymeric vehicle comprises a combination of a polyvinylpyrrolidone and a hydroxyalkylcellulose.

5. The formulation of claim 3, wherein the polymeric vehicle comprises a copolymer of methacrylic acid and methyl methylacrylate monomers.

6. The formulation of claim 4, wherein the hydroxyalkylcellulose is selected from hydroxymethylcellulose, hydroxyethylcellulose, and hydroxypropylcellulose.

7. A transdermal formulation consisting essentially of:
between about 1-12 wt %; aripiprazole;
between about 5-40 wt % of a glycol selected from hexylene glycol, propylene glycol, or a mixture thereof;
between about 10-25 wt % glycerol;
between about 0.5-10 wt % lauryl lactate;
between about 0.5-10 wt % lactic acid;
optionally, between about 2-15 wt % water or a surfactant; and
between 5-35 wt % of a polymeric vehicle comprising a polyvinylpyrrolidone or a hydroxyalkylcellulose or both,
wherein the formulation does not comprise any selected from N,N-dimethylformamide, N,N-dimethylacetamide, N-methyl-2-pyrrolidone, isopropyl myristate, diethyl sebacate, medium-chain triglyceride, and propylene carbonate.

8. The formulation of claim 7, wherein the surfactant is a sorbitan monolaurate.

9. The formulation of claim 7, wherein the hydroxyalkylcellulose is selected from hydroxymethylcellulose, hydroxyethylcellulose, and hydroxypropylcellulose.

10. The formulation of claim 7, wherein the polyvinylpyrrolidone is selected from polyvinylpyrrolidone homopolymers and polyvinylpyrrolidone copolymers.

11. A method for administering aripiprazole transdermally, comprising: providing a formulation according to claim 1 or 7 with instructions to apply the formulation to skin of a subject in need.

12. A method for treating depression, schizophrenia, or bipolar disorder comprising: providing a formulation according to claim 1 or 7 with instructions to apply the formulation to skin of a subject in need.

13. A transdermal delivery device, comprising: a formulation according to claim 1 or 7.

\* \* \* \* \*